(12) United States Patent
Cookson et al.

(10) Patent No.: US 6,991,938 B1
(45) Date of Patent: Jan. 31, 2006

(54) METHOD OF ASSAY

(75) Inventors: Alan Derek Cookson, Boston, MA (US); Phelim Daniels, Hounslow (GB)

(73) Assignee: Applied Research Systems ARS Holding N.V., Curacao (AN)

( * ) Notice: Subject to any disclaimer, the term of this patent is extended or adjusted under 35 U.S.C. 154(b) by 0 days.

(21) Appl. No.: 09/180,335

(22) PCT Filed: May 8, 1997

(86) PCT No.: PCT/GB97/01248

§ 371 (c)(1),
(2), (4) Date: Feb. 25, 1999

(87) PCT Pub. No.: WO97/43644

PCT Pub. Date: Nov. 20, 1997

(30) Foreign Application Priority Data

May 9, 1996 (GB) .............................. 9609653

(51) Int. Cl.
*G01N 21/64* (2006.01)

(52) U.S. Cl. ...................... 436/164; 436/172; 436/174; 422/82.11

(58) Field of Classification Search ................ 436/164, 436/172, 174; 422/82.11
See application file for complete search history.

(56) References Cited

U.S. PATENT DOCUMENTS

| 4,157,871 | A | * | 6/1979 | Anderson et al. ........... 356/338 |
| 4,368,047 | A |   | 1/1983 | Andrade |
| 4,399,099 | A | * | 8/1983 | Buckles ....................... 422/58 |
| 4,608,344 | A | * | 8/1986 | Carter et al. .................. 436/34 |
| 5,019,999 | A | * | 5/1991 | Swirski, Jr. ................. 356/339 |
| 5,120,662 | A |   | 6/1992 | Chan |
| 5,420,042 | A | * | 5/1995 | Schafer et al. .............. 436/164 |
| 5,753,518 | A | * | 5/1998 | Karlsson ..................... 436/517 |

FOREIGN PATENT DOCUMENTS

| DE | 0148463 | * | 7/1985 |
| EP | 0184600 | * | 6/1986 |
| EP | 0667528 | * | 8/1995 |
| WO | 90/14590 |  | 11/1990 |
| WO | 92/14136 |  | 8/1992 |

OTHER PUBLICATIONS

K.A. Davis, et al., "Continuous Liquid–Phase Piezoelectric Biosensor for Kinetic Immunoassay", Analytical Chemistry, vol. 61, 1989, pp. 1227–1230.

* cited by examiner

*Primary Examiner*—Jeffrey R. Snay
(74) *Attorney, Agent, or Firm*—Dickstein, Shapiro, Morin & Oshinsky, LLP.

(57) ABSTRACT

A kinetic assay method for quantifying an analyte in a sample.

13 Claims, 2 Drawing Sheets

METHOD OF ASSAY

The present invention relates to a method of assay for quantifying an analyte in a sample, in particular to a kinetic assay method during the course of which a component of the assay system becomes at least partly bound, directly or indirectly, to the surface of a solid body.

The method of the present invention has particular applicability in the field of immunoassays and will be described herein with particular reference to immunoassays; however the method can also be used in other assays which rely on the affinity between the species to be assayed (hereinafter "ligand") and a specific binding partner for the ligand (hereinafter "specific binding partner").

The ligand concentration in such systems may be determined by monitoring the extent of complex formation or rate at which complex formation occurs. One preferred way of achieving this is by conjugating an additional component having a measurable parameter to either the ligand or its specific binding partner. This additional component is known in the art as a label and various chemical and biochemical labels are known eg. radioisotopic or biochemiluminescent species, spin labels, fluorophores, chromophores, etc. In the course of such assays, the label in effect becomes bound, indirectly at least, to a solid surface.

Conventionally, most immunoassay systems of the type described above have relied upon there being washing and/or separation step(s) in the assay protocol in order to separate bound label from label remaining in solution; the latter otherwise would be free to interfere with the bound label and lead to inaccurate results. Once separation has been effected, a variety of known techniques may be used to quantify the bound label and thereby yield a measure of the concentration of ligand present in the sample under investigation. In such systems, the separation procedure must be repeated at each time (t) at which it is desired to make a measurement, rendering the method as a whole somewhat labour intensive and slow. In addition to these problems, there is a degree of arbitrariness in the estimation of the commencement of incubation of the assay which leads to errors in the overall timing.

In order to speed up reading the assay and/or to increase the sensitivity of conventional assay systems, it would be desirable to make kinetic measurements. The limitations referred to above mean that conventional assay systems do not lend themselves to making reliable kinetic measurements and it has been done in only a very few cases where the characteristics of the assay system allow. For example, it is known to make kinetic measurements in immunoassay systems in which enzymes are the label of choice, the rate of evolution of the product of the enzyme catalysed reaction being the parameter which is measured. In this case, measurement of the enzyme label only shortens the duration of the signal generation step and has no impact on the time taken to measure antibody:antigen binding i.e. the kinetic measurement applies to the final step of the assay and not to the key immune reaction.

Kinetic measurements have also been used in certain immunosensors. Here the rate of change of signal of the sample containing an unknown quantity of antigen is measured and compared with the same parameter for standards containing known concentration of antigen. The most convenient way of achieving this is to construct a curve of rate of change of signal (dI/dt in measurands per unit time) versus known concentration of antigen in the standard. In this way, dI/dt for the sample of interest may simply be read off the standard curve to arrive at the unknown antigen concentration. Naturally, such a technique suffers the drawback that the assay must be allowed to attain an arbitrarily determined equilibrium at which point a single end-point measurement of the signal is made. The speed with which equilibrium is reached may be prohibitively slow and this in itself can introduce errors in the measured rate of change of signal which will be critically dependent on the prevailing conditions (eg. temperature, viscosity). Clearly it is not possible in such a system to obtain quick and accurate measurements of the ligand concentration.

Kinetic measurements have also been used to determine the concentration of an unknown in some immunoassays, as disclosed in EP-A-667528 (Daikin Industries, Limited). However, such assays do not involve the continuous monitoring of the concentration of the unknown.

In other assays systems, for example that disclosed in EP-A-184600 (Battelle Memorial Institute) kinetic measurements may be made, but are not used to determine the concentration of an unknown in a sample, with instead a single final measurement being used in this regard.

The present invention is based on the finding that, in assay methods, during the course of which a component of the assay system becomes directly or indirectly bound to, or adsorbed on, the surface of a solid body, a reliable measurement of said bound or adsorbed component (ie. without interference from the free component in solution) can be obtained by direct and continuous monitoring of said component.

It should be emphasised that the method of the invention relates to assay systems of both the direct and indirect variety, the only requirement being that they involve the binding of a component of the assay system to the surface of a solid body. Direct assay methods may typically involve monitoring the reflected and/or generated signal within an irradiated solid optical structure (eg. a waveguide) in order to determine the extent to which (or the rate at which) the optical characteristics of said optical structure and/or the generated signal are altered by the biochemical complexation of a ligand and specific binding partner which is bound to said optical structure (eg. antigen/antibody complexation). Indirect assay methods may typically involve monitoring a label (eg. a fluorophore) bound to one or more of the components present in the assay and directly or indirectly to the solid body. Such methods are described for example in inter alia WO-A-88/07202 and WO-A-90/01166 (Ares Serono). The invention is equally applicable to displacement assays where the labelled component is removed from the solid surface as a result of the antibody: antigen interaction.

The novel assay method of the present invention has the advantage that an indication of the unknown ligand concentration may be obtained at a very early stage of the incubation period without the need to wait for some arbitrarily determined end-point such as equilibrium. Moreover, the operator is able to observe the result continuously and judge whether it would be worthwhile taking further readings in an attempt to improve the accuracy of the result. Additionally, continuous monitoring allows random errors caused by, for example, problems with instrumentation to be readily identified. Any spurious result may simply be isolated and ignored.

Thus in its broadest aspect the present invention provides the use of kinetic measurements to determine quantitatively an unknown sample in an assay system in which a component thereof becomes at least partly bound directly or indirectly to the surface of a solid body, for example the surface of a solid optical waveguide, electrode or piezoelectric crystal.

By "kinetic measurements" are meant direct and continuous measurements of a measurable property or effect associated with said bound component (hereinafter an "analyte dependent parameter") at a time before the assay reaches a substantially steady state i.e. equilibrium.

Viewed from a further aspect, the present invention provides a method of assay in which a component becomes at least partly bound, directly or indirectly, to a solid body, for example an optical waveguide, electrode or piezoelectric crystal, characterised in that an analyte-dependent parameter associated with said component at said solid body is measured in a direct and continuous manner and in that said measured analyte dependent parameters are manipulated to quantitatively determine an unknown sample. In one embodiment the analyte dependent parameter is an analyte dependent optical parameter (i.e. a measurable optical property or effect) but parameters relating to electrochemical or piezoelectric properties/effects may be used.

In a further embodiment, the use or method according to the invention may be applied to an analyte of known concentration for the purposes of calibration.

In a particular preferred embodiment, said method comprises the steps of:

(a) calibrating the assay system for x samples each of known analyte concentration ($C_a$) by measuring continuously for each sample independently at a plurality of times ($t_y$) after the onset of incubation the value of an analyte-dependent parameter ($P_z$), (b) for an analyte of unknown concentration ($C_b$) measuring continuously n independent values of an analyte-dependent parameter ($P_d$) each at time $t_e$ after the onset of incubation, (c) combining the data ($P_d, t_e$) from step (b) with the calibration data ($P_z, t_y, C_a$) from step (a) to calculate the unknown dose of analyte ($C_b$) at time $t_a$.

The analyte-dependent parameter referred to above may conveniently be any parameter associated with the interaction between applied radiation and the relevant bound assay component and includes but is not limited to light-absorbing, scattering, fluorescence emission, phosphorescence emission, luminescence emission (including chemiluminescence, bioluminescence and electrochemiluminescence) or colour emission properties. The term is also intended to encompass the measurable effects which the bound component may have for example on the refractive index or transmittability of the optical surface, on total internal reflection or surface plasmon resonance (SPR) within the solid optical body, or interactions with evanescent waves at the surface of the body. Devices and techniques for measuring such analyte dependent optical parameters or manipulating the above-mentioned effects are known in the art.

The invention also extends to the use of nonoptical devices such as electrochemical and other sensor devices (e.g. piezoelectric crystals).

As used herein, the term "solid body" is intended to refer appropriately to any of the known surfaces to which may usefully be bound ligand and/or specific binding partner components eg. in the form of an electrochemical, optical, piezoelectric or fibre-optic biosensor as described in U.S. Pat. No. 5,356,780 or an optical structure capable of exhibiting an SPR effect (eg. a diffraction grating) or a transparent optical body (eg. a prism, sheet or fibre acting as a waveguide such as is described in EP-A-170376 (Unilever)) of the type described in EP-A-171148 (Unilever) and WO-A-95/24632 (Applied Research Systems). In electrochemical assay devices where the solid body is an electrode, it is known to use components bound to magnetic beads or particles which may be attracted to a magnetic field created at the electrode. These devices too are useful in the method of the invention and are described in for example EP-A-170446 (Serono Diagnostics Limited).

In one embodiment of the invention, the solid body may be coated with a specific binding partner to the analyte of interest. Specific binding partners may be coated onto the surface of the solid body by known techniques, for example, as described in EP-A-171148.

The invention is particularly suited to assay methods during the course of which a component acting as a label and having optically measurable properties such as light absorbing, light-transmitting, light scattering, fluorescent, phosphorescent, luminescent or colour properties becomes at least partly bound (directly or indirectly) to the surface of a transparent solid body (eg. an optical waveguide), especially methods of the type described in, for example, EP-A170376 and EP-A-171148.

In embodiments of the invention which relate to indirect assay techniques, the binding of labels directly or indirectly to one or other of the ligand or its specific binding partner may be carried out by methods well known to the skilled man. The identity of such labels is similarly well-known to the skilled man and includes those mentioned hereinbefore.

The method according to the invention is, in certain embodiments, intended for use in specific binding assay procedures in chemical, biochemical or clinical test procedures, in particular to immunoassay procedures. Examples of such procedures are described in inter alia EP-A-0171148, WO-A-92/09892, WO-A-93/25892 and WO-A-93/25908.

The present method is also applicable to a wide variety of devices provided these are of a type which make use of a component bound to a solid body including, for example, dip-stick or test-strip sensors, devices using a "sample flow-through" configuration or devices employing sample containment. Sample containment devices are preferred for carrying out the method of the invention, with a more preferred device being a capillary fill device, especially a fluorescence capillary device, for example the type of device described in EP-A-171148, WO-A-90/14590 or in International patent application No. PCT/GB95/02236 (Applied Research Systems ARS Holding NV Such capillary fill devices may be used singly or in a suitable holder such as is described in WO-A-90/1830.

In carrying out the method according to the invention to determine an unknown sample, it is first necessary to calibrate the instrument using a set of solutions containing known concentrations of analyte (ie. step (a) as defined hereinbefore). The protocol adopted for this step may be conveniently chosen by the operator and is in no way intended to restrict the scope of the invention. Such operator determined variables include the number of standards (referred to as x above) which might typically be three or more, the number of devices, the number of readings, the time interval between readings and the total period over which calibration is carried out.

After filling a device with a particular standard, measurements of the analyte dependent parameter (referred to more generally as $P_z$ above) are taken at regular intervals, such as every five seconds, for as long as is appropriate. This procedure is optionally repeated for further devices, yielding response data at each time point (referred to as $t_y$ above) for all of the standard analytes. For each time point $t_{y/A}$ it is, therefore, possible to produce a standard curve of $P_z$ vs $C_a$ (appropriate to time $t_y$). In one embodiment, the ($P_z, C_a$) data may be fitted to a standard equation such as an n parameter logistic equation, or appropriate algorithm, using any conventional fitting method such as a least squares method.

In step (b) of the method according to the invention, the unknown analyte-dependent parameter (referred to as $P_d$ above) may be measured at any time-point (referred to as $t_e$ above) and used to determine a concentration by interpolation from the standard curve ($P_z$, $C_a$) for that time point. Appropriate smoothing software may be used to improve the accuracy of the estimation of concentration of analyte in the sample. Typically the ($t_e$, $C_b$) data obtained in this step are manipulated to give a dose versus time profile for the sample, an example of which is given in FIG. 2.

As has previously been emphasised, the method according to the invention is a kinetic method and in step (b) the interval between readings is operator determined and is typically of the order of less than 60s, particularly less than 30s, especially less than 10s and more especially 5s or less.

In practice, it is envisaged that the calibration data from step (a) of the method according to the invention may be prepared by a manufacturer for each batch of reagents and presented as a series of standard kinetic curves. These curves would then be supplied to the customer via convenient means for storing machine readable encoded data such as software, bar codes or magnetic strips for each batch of reagents. Thus, for example, on running unknown samples, the appropriate instrument would carry the calibration curves in its software and use them as "look up tables" in order to calculate the dose of analyte in the sample under test.

Thus in a further aspect the present invention provides a method of calibrating an assay system comprising step (a) as hereinbefore defined and optionally thereafter fitting the ($P_z$, $C_a$) data to a standard equation (appropriate to time $t_y$). A kit comprising an assay device together with means for storing machine readable encoded data which contains calibration data $P_z$, $t_y$, $C_a$ as hereinbefore defined and which is adapted to cooperate with reading means for the purpose of quantitatively determining an unknown analyte forms a further aspect of the invention.

One technological area which has undergone significant advancement in recent years is the so-called point-of-care assay systems. These rely on very accurate, sensitive and rapid methods of assay to enable successful near patient testing to be performed. Clearly therefore the present invention, with the advantages referred to hereinbefore, lends itself to such technology.

The method of the invention is particularly applicable to assays of antigens or antibodies, i.e. to immunoassays, and in one embodiment of the invention the ligand under assay is an antigen and the specific binding partner comprises an antibody to the said antigen. However, as mentioned above, the invention is not to be taken as limited to assays of antibodies or antigens. Examples of ligands which may be assayed by the improved assay method of the invention are given in Table 1 below, together with an indication of a suitable specific binding partner in each instance.

TABLE 1

| Ligand | Specific Binding Partner |
| --- | --- |
| antigen | specific antibody |
| antibody | antigen |
| hormone | hormone receptor |
| hormone receptor | hormone |

TABLE 1-continued

| Ligand | Specific Binding Partner |
| --- | --- |
| polynucleotide strand | complementary polynucleotide strand |
| avidin | biotin |
| biotin | avidin |
| protein A | immunoglobulin |
| immunoglobulin | protein A |
| enzyme | enzyme cofactor (substrate) or inhibitor |
| enzyme cofactor (substrate) or inhibitor | enzyme |
| lectins | specific carbohydrate |
| specific carbohydrate of lectins | lectins |

The method of the invention has very broad applicability but in particular may be used in assays for: hormones, including peptide hormones (e.g. thyroid stimulating hormone (TSH), luteinizing hormone (LH), human chorionic gonadotrophin (hCG), follicle stimulating hormone (FSH), insulin and prolactin) or non-peptide hormones (e.g. steroid hormones such as cortisol, estradiol, progesterone and testosterone, or thyroid hormones such as thyroxine (T4) and triiodothyronine), proteins (e.g. carcinoembryonic antigen (CEA) and antibodies, alphafetoprotein (AFP) and prostate specific antigen (PSA)), drugs (e.g. digoxin, drugs of abuse), sugars, toxins, vitamins, viruses such as influenza, para-influenza, adeno-, hepatitis, respiratory and AIDS viruses, virus-like particles or microorganisms.

It will be understood that the term "antibody" used herein includes within its scope:
(a) any of the various classes or sub-classes of immunoglobulin, e.g. IgG, IgA, IgM, or IgE derived from any of the animals conventionally used, e.g. sheep, rabbits, goats or mice,
(b) monoclonal antibodies,
(c) intact molecules or "fragments" of antibodies, monoclonal or polyclonal, the fragments being those which contain the binding region of the antibody, i.e. fragments devoid of the Fc portion (e.g. Fab, Fab', F(ab')$_2$), the so-called "half-molecule" fragments obtained by reductive cleavage of the disulphide bonds connecting the heavy chain components in the intact antibody or fragments obtained by synthetic methods,
(d) antibodies produced or modified by recombinant DNA techniques, including "humanised antibodies".

The method of preparation of fragments of antibodies is well known in the art and will not be described herein.

The term "antigen" as used herein will be understood to include both permanently antigenic species (for example, proteins, peptides, bacteria, bacterial fragments, cells, cell fragments and viruses) and haptens which may be rendered antigenic under suitable conditions.

The method of the present invention is applicable to the normal range of sample types e.g. urine, serumbased and whole-blood samples, food samples such as water samples and milk samples and to the known range of assay types, for example competition or sandwich assays including inter alia direct antigen assays, competitive antigen assays, direct antibody assays, sandwich antibody assays, linked antibody assays, competitive antibody assays and the like.

The detailed preparation of the assay devices within the scope of the method according to the invention and the assay procedures used to collect the data are well known to the skilled man.

The invention will now be illustrated in a nonlimiting fashion by the following Examples.

EXAMPLES

Example A

Figure 1:
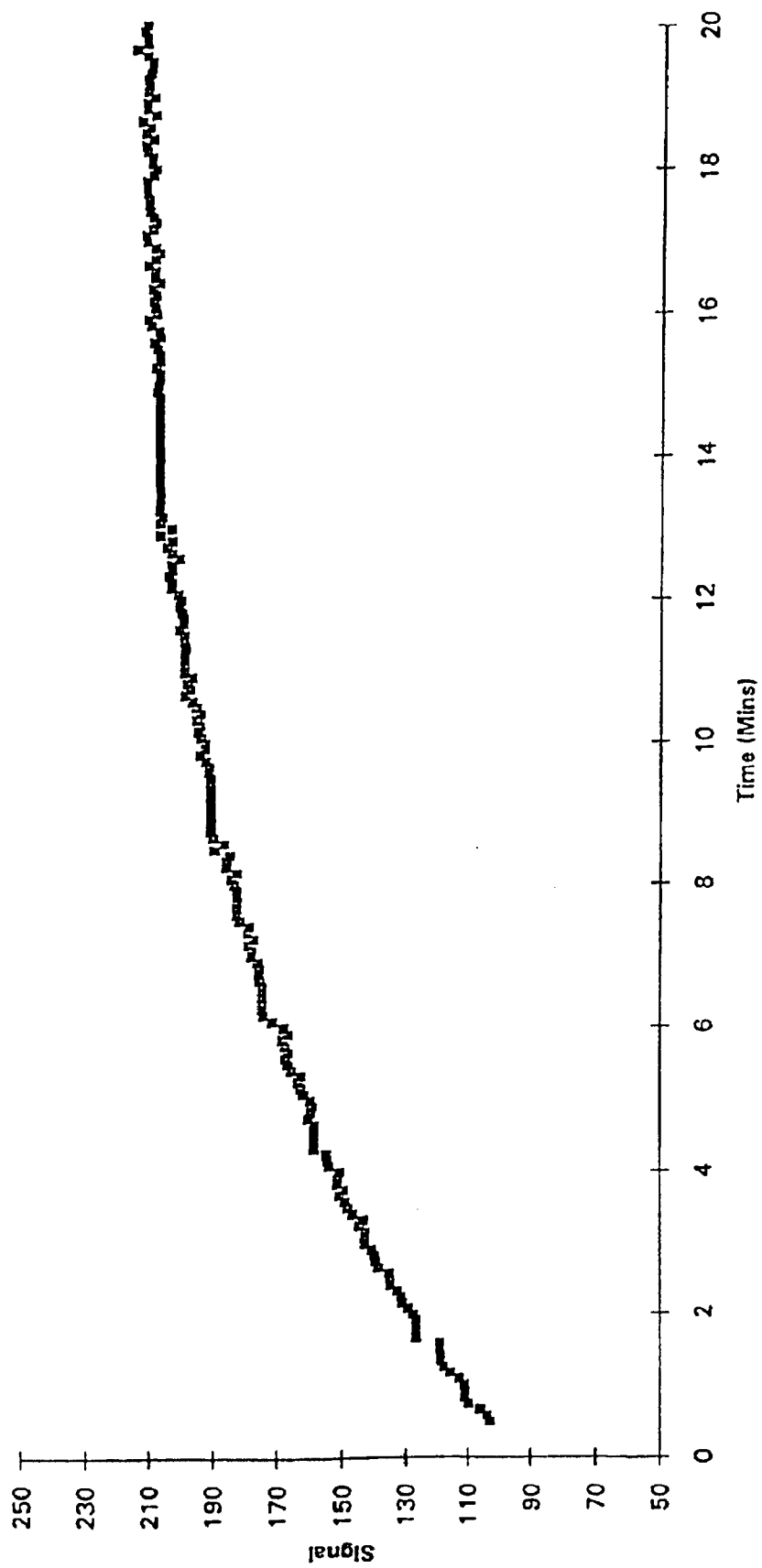
FIG. 1 shows the kinetic signal of a reaction standard.

1. Preparation of starting materials:

1.1 Fabrication of antibody-coated optical waveguides:

Anti-PSA monoclonal antibodies were supplied by Serono Diagnostics S A, Coinsins, Switzerland. A sheet of Permabloc glass (Pilkington Glass Ltd., St. Helens, UK) having a thickness of about 1 mm was cleaned with detergent (eg. Tween 20) in ultra-pure water with ultrasonic agitation. The surface of the glass was activated by incubating it in a 2% solution of aminopropyltrimethoxysilane in water (pH 3–4) for two hours at 75° C. After rinsing in water, the glass sheet was dried at 115° C. for at least four hours. The glass was then incubated for 60 minutes in a 2.5% solution of glutaraldehyde in a 0.05M phosphate buffer (pH 7) and then washed thoroughly with distilled water. Anti-PSA antibody was patterned onto the glass by discretely dosing a 1% solution of the antibody in phosphate buffer (pH 7) onto the glass and incubating it for 2 to 4 hours after which the glass sheet was washed with buffer solution. Unwanted adsorbed protein was removed by soaking with 6M urea solution in a known manner. Finally a layer of sucrose/lactose was formed over the surface of the glass sheet by spin coating. This formed plate 4 of the FCFD test device.

1.2 Preparation of PSA conjugated to allophycocyanin (APC):

A second anti-PSA monoclonal antibody, which recognises a different epitope on the PSA molecule to the one used in 1.1 above, was conjugated to allophycocyanin ($\lambda$ex=650 nm, $\lambda$em=660 nm) by Molecular Probes Inc., Eugene, Oregon, USA and was used as supplied.

1.3 Microdosing of the specific reagents over a discrete zone of anti-PSA antibody:

An opaque coating was screen printed onto a clean sheet of Permabloc glass as described in GB 8911462.3. The measurement zone of the device was fabricated by microdosing a layer of anti-PSA/allophycocyanin antibody conjugate in buffer containing polyvinyl alcohol in an area 3×7 mm onto the glass over the zone. After the conjugate was air dried, a layer of polyvinyl alcohol (4% in buffer) was microdosed over the conjugate. Finally the whole sheet of glass was coated in a layer of sucrose/lactose by spray coating. This formed plate 2 of the FCFD test device.

1.4 Fabrication of FCFD test devices:

FCFD test devices such as have been described in EP-A0171148 were fabricated by screen printing onto the waveguide resulting from 1.1 above bonding tracks of an ultraviolet curing glue (UVS 91, Norland Inc., USA) containing glass microspheres of 100 $\mu$m diameter (Jencons Ltd., UK) in a pattern defining the long edges of the capillary cell devices. A sheet of glass as defined in 1.3 above was then placed over the waveguide and a vacuum applied to the laminate. As a result of the vacuum, the upper sheet of glass was caused to press down onto the glue, the glass microspheres defining a gap of 100 $\mu$m between the glass sheets. The laminate was then exposed to an ultraviolet light source to cure the glue. Finally, the laminate sheet was broken into individual test devices as described in EP-A-0171148.

1.5 Apparatus used in the measurement of the PSA assay:

A simple fluorimetry apparatus comprising a continuous light source (provided by light emitting diodes which emit light at a suitable wavelength to excite the allophycocyanin fluorophore) and a photomultiplier tube (PMT). Light emerging from the optical edge of the FCFD is filtered to remove stray pump light and the discrete angle range required to read the bound fluorescence measured by focusing the light onto the PMT through an aperture.

2. Assay Procedure for PSA:

Signals indicative of analyte concentration were obtained from the FCFD devices by the following method. The device, containing the sample to be assayed, was flood illuminated with light appropriate to stimulate the fluorophore contained within the test reagentry. This input light is continuous and its intensity is repeatable at every required measurement time point.

In estimating the concentration of an unknown sample, it is first necessary to calibrate the instrument using a set of solutions containing known concentrations of analyte. For the data presented here, seven standard concentrations were used, each concentration being run in duplicate devices. After filling a device with a particular standard concentration, measurements of the level of fluorescence were taken at regular intervals (every 5 seconds for the data presented). In this way the kinetics of the reaction could be monitored, as demonstrated in FIG. 1. Measurements were taken over a period of 20 minutes. After completing kinetic measurements on all devices, data was available (at all of the time points) regarding the response to all the particular standard analyte concentrations. It was therefore possible to produce a "standard curve" corresponding to each of the time points. In the case of the present data the standard equation used was a four parameter logistic, having been fitted by a conventional least squares method.

Figure 2:
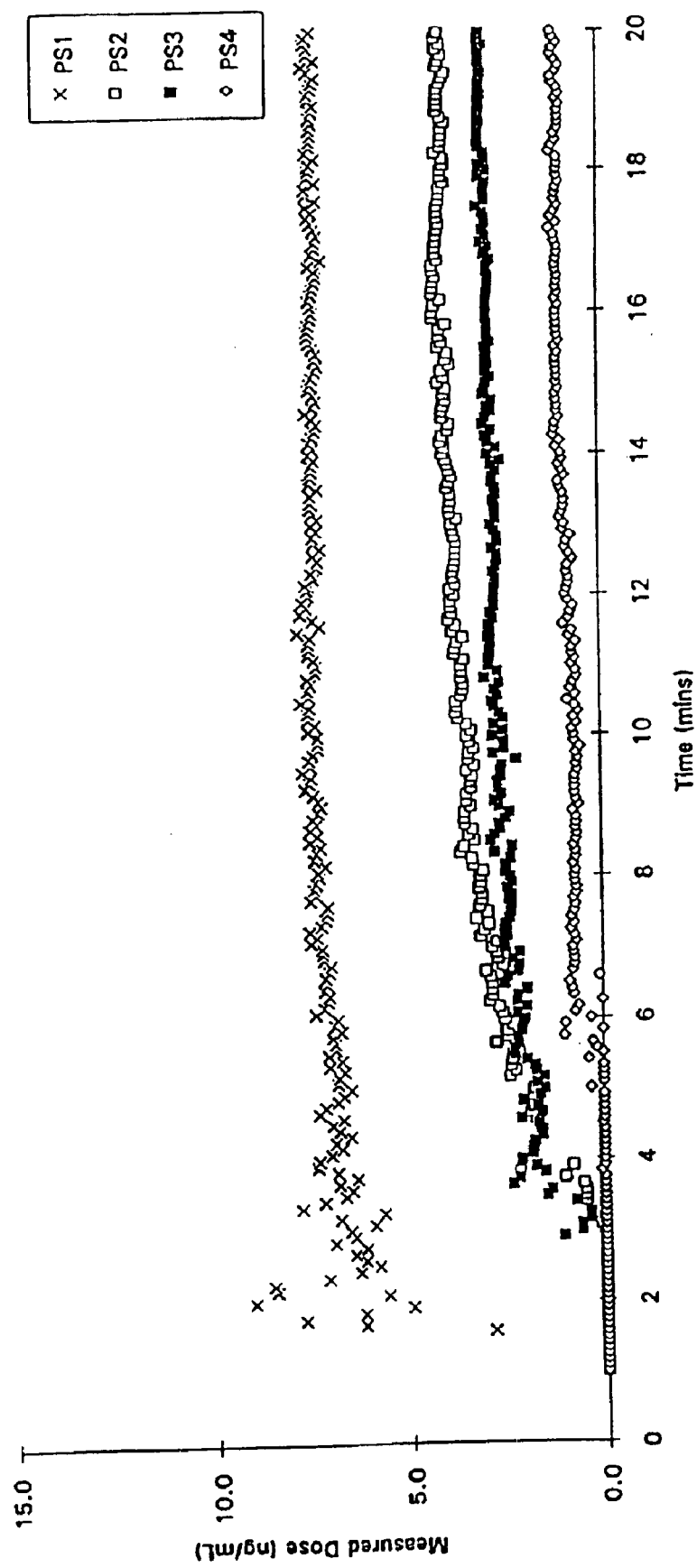
FIG. 2 shows the results of the dependence of a measured dose on assay time interpolated from a relevant standard.

Subsequent to this calibration procedure, samples of unknown concentration were run in the same kinetics mode. The fluorescence level at any time-point was interpolated off the associated standard curve enabling a concentration level to be ascertained. The results of the dependence of the measured dose on assay time interpolated from the relevant standard curve are shown in FIG. 2.

What is claimed is:

1. A method of assay in which a component becomes at least partly bound to a solid body characterised in that an analyte dependent parameter associated with said component is kinetically measured in a direct and continuous manner and the resulting measured analyte dependent kinetic data is continuously manipulated to continuously quantitatively determine an unknown sample for a period of time after the onset of incubation and before the assay reaches a substantially steady state.

2. A method as claimed in claim 1 wherein said solid body is an optical waveguide.

3. A method as claimed in claim 1 wherein said analyte dependent kinetic data is an optical parameter.

4. A method as claimed in claim 3 wherein said optical parameter is fluorescence emission.

5. A method as claimed in claim 4 wherein said solid body is in the form of a sample containment device.

6. A method as claimed in claim 5 wherein said device is a capillary fill device.

7. A method as claimed in claim 1 comprising the steps of
   (a) calibrating the assay system for a number x of samples, each of known analyte concentration ($C_a$), by measuring continuously for each sample independently at a plurality of times ($t_y$) after the onset of incubation the value of said analyte-dependent kinetic data ($P_z$),
   (b) for an analyte of unknown concentration ($C_b$) measuring continuously a number n of independent values of said analyte-dependent parameter ($P_d$) each at time $t_e$ after the onset of incubation, (c) combining the data ($P_d$, $t_e$) from step (b) with the calibration data ($P_z$, $t_y$, $C_a$) from step (a) to calculate the unknown dose of analyte ($C_b$) at time $t_e$.

8. A method as claimed in claim 2 wherein said kinetic data is fluorescence emission.

9. A method as claimed in claim 1 wherein said solid body is in the form of a sample containment device.

10. A method as claimed in claim 9 wherein said device is a capillary fill device.

11. A method as claimed in claim 1 wherein said kinetic measurement, data manipulation and determination monitoring are continued until the assay is considered to have reached a substantial steady state.

12. A method as claimed in claim 1 wherein said kinetic measurement, data manipulation and determination monitoring are discontinued before the assay reaches a substantial steady state.

13. A method of assay in which a component becomes at least partly bound to a solid body, the assay having been calibrated for number x of samples, each of known analyte concentration ($C_a$), by measuring continuously for each sample independently at a plurality of times (ty) after the onset of incubation the value of an analyte-dependent parameter ($P_z$), characterized in that the method comprises the steps:

for an analyte of unknown concentration ($C_b$) measuring in a direct and continuous manner a number n of independent values of an analyte-dependent parameter ($P_d$) which is associated with said component each at time $t_e$ after the onset of incubation, and manipulating said measured analyte dependent parameter to continuously quantatively determine an unknown sample for a period of time after the onset of incubation and before the assay reaches a substantially steady state by combining the data ($P_d$, $t_e$) with the calibration data ($P_z$, $t_y$, $C_a$) to calculate the unknown dose of analyte ($C_b$) at time $t_e$.

* * * * *